United States Patent [19]
Cameron et al.

[11] Patent Number: 5,670,343
[45] Date of Patent: Sep. 23, 1997

[54] CLONING AND/OR EXPRESSION VECTORS, PREPARATION METHOD AND THEIR USE

[75] Inventors: Beatrice Cameron; Joel Crouzet; Sophie Levy-Schil, all of Paris, France

[73] Assignee: Rhone Poulenc Biochimie, Antony, France

[21] Appl. No.: 330,621

[22] Filed: Oct. 28, 1994

Related U.S. Application Data

[63] Continuation of Ser. No. 938,242, filed as PCT/FR91/00333, Apr. 23, 1991, published as WO91/16439, Oct. 31, 1991, abandoned.

[30] Foreign Application Priority Data

Apr. 24, 1990 [FR] France .................................. 90 05185

[51] Int. Cl.$^6$ .............................. C12P 21/00; C12N 5/10; C12N 15/63
[52] U.S. Cl. .................. 435/71.2; 435/172.3; 435/252.3; 435/320.1
[58] Field of Search ............................ 435/320.1, 69.1, 435/71.2, 172.3, 252.3, 29

[56] References Cited

U.S. PATENT DOCUMENTS

| 4,590,163 | 5/1986 | Helinski et al. ........................ 435/317 |
| 4,760,022 | 7/1988 | Molin et al. ........................... 435/320 |

OTHER PUBLICATIONS

Schmidhouser et al 1985 J Bacteriology 164: 446–455.
Dictionary of Microbiology and Molecular Biology, 1988, John Wiley & Sons, Singleton et al (eds.) pp. 220–223, 337 and 902.
Journal of Biotechnology, "Mapping and cloning of the par-region of broad-host-range plasmid RP4", Saurugger, et al., V. 4, 1986, 333–343.

*Primary Examiner*—Elizabeth McElwain
*Attorney, Agent, or Firm*—Finnegan, Henderson, Farabow, Garrett & Dunner, L.L.P.

[57] ABSTRACT

The present invention relates to new cloning and/or expression vectors having a broad host range in Gram-negative bacteria, in particular, in the production of recombinant proteins or of metabolites, or in bioconversion reactions, as well as to the host cells containing such vectors.

12 Claims, 4 Drawing Sheets

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 22
( B ) TYPE: NUCLEIC ACID
( C ) STRANDEDNESS: SINGLE
( D ) TOPOLOGY: LINEAR ( i i ) MOLECULE TYPE:
( A ) DESCRIPTION: OLIGONUCLEOTIDE ( i i i ) HYPOTHETICAL: NO ( i x ) FEATURE:
( A ) NAME/KEY:
( B ) LOCATION:
( C ) IDENTIFICATION METHOD:
( D ) OTHER INFORMATION: OLIGONUCLEOTIDE, AS SHOWN IN FIGURE 2.

( x i ) SEQUENCE DESCRIPTION: SEQ ID NO: 1:

CCCGTTGAGC TCCGCCAGGT GC    22

( 2 ) INFORMATION FOR SEQ ID NO: 2:

( i ) SEQUENCE CHARACTERISTICS:
( A ) LENGTH: 112
( B ) TYPE: NUCLEIC ACID
( C ) STRANDEDNESS: DOUBLE
( D ) TOPOLOGY: LINEAR ( i i ) MOLECULE TYPE:
( A ) DESCRIPTION: OLIGONUCLEOTIDE ( i i i ) HYPOTHETICAL: No ( i x ) FEATURE:
( A ) NAME/KEY: MOB LOCUS
( B ) LOCATION:
( C ) IDENTIFICATION METHOD:
( D ) OTHER INFORMATION: ORIGIN OF TRANSFER OF RK2

( x i ) SEQUENCE DESCRIPTION: SEQ ID NO: 2:

CCGGCCAGCC TCGCAGAGCA GGATTCCCGT TGAGCACCGC CAGGTGCGAA TAAGGGACAG    60

TGAAGAAGGA ACACCCGCTC GCGGGTGGGC CTACTTCACC TATCCTGCCC GG    112

CLONING AND/OR EXPRESSION VECTORS, PREPARATION METHOD AND THEIR USE

This is a continuation of application Ser. No. 07/938,242, filed as PCT/FR91/00333, Apr. 23, 1991 published as WO91/16439, Oct. 31, 1991, now abandoned.

FIELD OF THE INVENTION

The present invention relates to new cloning and/or expression vectors having a broad host range in Gram-negative bacteria. It also relates to the use of these vectors, in particular in the production of recombinant proteins or of metabolites, or in bioconversion reactions, as well as to the host cells containing such vectors.

BACKGROUND OF THE INVENTION

Recent progress in molecular biology has led to the development of new vectors which can be used in genetic engineering methods, possessing a broad host range. These vectors contrast with those having a narrow host specificity, such as ColE1, in the ubiquitous character, from a taxonomic standpoint, of the hosts in which they replicate. This character is very marked in the case of some plasmids which replicate in almost all Gram-negative bacteria. Such plasmids possess the distinctive feature of being able to be used in bacteria such as *Escherichia coli* in order to make the necessary constructions, and then to be directly introduced into the Gram-negative host which has been chosen. Another feature of these vectors lies in the property they possess of either mobilizing or being mobilized for conjugative transfer from a donor bacterium to a recipient bacterium. These conjugated transfers generally take place with a very high frequency (between 1 and $10^{-2}$), considerably higher than known transformation systems.

The plasmids having a broad host range in Gram-negative bacteria described in the literature belong to the incompatibility groups C, N, P, Q and W (incC, incN, incP, incQ and incW). Among these, the plasmids of incompatibility groups P and Q are those studied most satisfactorily and those for which a large number of derivatives have been constructed (Schmidhauser et al., 1988). They are also the ones which are used almost exclusively. In this connection, it is described that these plasmids replicate in all the Gram-negative bacteria studied except for *Myxococcus xanthus*, *Bradyrhizobiam japonicum* and bacteria of the genus Bacteroides (Kües and Stahl, 1989). Plasmids of the incompatibility group W are used marginally, on the one hand because they possess fewer advantages than plasmids of the incompatibility groups P and Q, and on the other hand because they are less well known.

The incompatibility group P is divided into subgroups: incPα and incPβ, the plasmids studied most intensively being RK2, RP4 (which are, in fact,.two independent isolates of the same plasmid) and R751. These plasmids possess the feature of being self-conjugative, that is to say they carry the conjugation functions (tra and mob). Furthermore, they are large (RK2 is 60 kb in size), low copy number (RK2 has a copy number of between 4 and 7 in *E. coli*) plasmids.

The replication of these plasmids has been studied in detail by Kües and Stahl. Thus, the origin of replication oriV is known to be composed of (i) 8 17-bp segments, (ii) a putative promoter surrounded by binding sites for the DnaA protein of *E. coli* and a putative binding site for the IHF protein of *E. coli*, (iii) a 9-bp AT-rich sequence followed by a binding site for the DnaA protein, and then (iv) a GC-rich region. The origin of replication associated with the trfA gene, which is translated into two proteins A1 and A2 encoded by the same frame but which are initiated at different codons, constitutes a replicon which has the same widespread occurrence as RK2. Depending on the host, either A2 appears necessary for replication, or A1 and A2 are both essential (Thomas, 1986). The replication of these plasmids is controlled by a complex regulation network in which the kil and kor genes participate. The kor for (kil-override) genes antagonize the lethal effect of kil genes (kilA, kilB, kilC and kilD), and negatively regulate the expression of trfA. Five kor genes have been identified (korA, korB, korC, korE and korF). The network of regulation of these genes among themselves and with trfA is recognised as permitting adaptation of the RK2 replicon to the host in which it replicates (Kües and Stahl, 1989). Schmidhauser and Helinski (1985) also showed that deletion of some of these genes resulted in some hosts in a lower segregational stability.

It is hence apparent that all these genes are necessary in order to observe the best possible stability of RK2 or RP4 derivatives.

Several RK2 derivatives have been constructed as multi-host vectors. They are plasmids which have retained the tetracycline resistance gene of the initial vector since this gene is located close to the origin of replication (oriV). The plasmids in question are, for example, pRK290, pRK404 and pRK415 (Ditta et al., 1980 and 1985, Keen et al., 1988, Schmidhauser et al., 1988). Among these, plasmid pRK290 (Ditta et al., 1980) will be mentioned more especially, this plasmid showing properties of great stability in a large number of Gram-negative bacteria (Schmidhauser and Helinski, 1985). This plasmid is maintained stably in *Escherichia coli*, Azotobacter, *Pseudomonas putida*, *Rhizobium meliloti* and *Rhodopseudomonas sphaeroides*. However, in other Gram-negative bacteria, this same plasmid is not as stable; this applies to *Agrobacterium tumefaciens*, Acetinobacter, Caulobacter and *Pseudomonas aeruginosa* (Schmidhauser and Helinski, 1985). Plasmid pRK290 is 20 kb in size, which is large for a cloning vector. It was obtained by a series of successive deletions starting from RK2. Apart from the transfer functions (tra genes), the kanamycin resistance gene and the transposon Tn1, these deletions have removed the kilA and kilC, korC and korE functions (Schmidhauser and Helinski, 1985). Hence it seems to be possible to observe some degree of stability in an RK2 derivative despite the loss of some kil and kor functions. However, it was observed that loss of Just the kilB function manifested itself in a marked decrease in the stability of the plasmid in several Gram-negative bacteria, and that all the RK2 derivatives tested and which were smaller in size than pRK290 were markedly less stable (Schmidhauser and Helinski, 1985).

Apart from the studies which have brought to light the respective importance of the different determinants of RK2 involved in the system of regulation of expression of trfA, a fragment which may be responsible for the segregational stability of these plasmids has been found (Sauruger et al., 1986). This fragment, positioned between the tra2 region and the kanamycin resistance gene, codes for a partition system (par). It was shown that this fragment was capable of stabilising plasmids pBR322 and pACYC177 in *Escherichia coli*. (Sauruger et al., 1986).

As regards the natural plasmids of the incompatibility group Q, RSF1010, R1162 and R300B, for example, may be mentioned. These plasmids have a copy number of between 10 and 60, depending on the microorganism. The size of these plasmids is much smaller than that of the plasmids of the incompatibility group P; in effect, it is less than 10 kb.

There is a region necessary in cis for the replication of these plasmids which comprises two subregions: (i) a region composed of 3.5 repeat sequences, of 40 bp rich in AT, of 60 bp rich in GC and of a putative box for binding the DnaA protein of E. coli; (ii) and on the other hand, a region with an inverted repeat sequence which can form a secondary structure with a stem of 40 to 60 bp. The initiation of replication of RSF1010 necessitates the presence of three proteins encoded by the plasmid: RepA, RepB and RepC, encoded by the repA, repB and repC genes. RepC recognises the origin of replication (in the repeat sequences) and regulates positively the initiation of replication; RepA has helicase activity; RepB and RepB* (which correspond to two proteins encoded by the same frame but each initiated at a different codon) have RSF1010-specific primase activity in vitro. The replication of RSF1010 is dependent on DNA polymerase III and the gyrase of the host. RSF1010 may be mobilized from one Gram-negative bacterium to another Gram-negative bacterium by the tra functions of the plasmids of the incompatibility groups IncIα, IncM, IncX and most especially IncP (Derbyshire and Willets, 1987).

No study relating to the stability of RSF1010 and its derivatives has been described to date. Furthermore, although the sequence of RSF1010 is known (Scholz and Scherzinger, 1989), no determinant of plasmid stability could be identified, either by functional analysis or by molecular analysis. There is every reason to believe that the plasmids of the incompatibility group Q are not as stable as those of the incompatibility group P.

In spite of these investigations, the known broad host range plasmids possess a number of drawbacks relating to their efficacy and to their application at industrial level.

In particular, for industrial use, independently of the host bacterium, plasmid vectors must possess a number of properties which correspond to operational constraints and constraints of biosafety.

The operational constraints are linked essentially to the segregational stability of the plasmid. In effect, it is very desirable to be able to avoid the use on an industrial scale of antibiotics in order to counterselect the loss of the plasmid. From this standpoint, a vector for industrial use must possess great segregational stability. This stability must be great over at least 25 successive generations, which represent the number of generations needed to go from the state of preservation of the recombinant strain to the end of a 200-m$^3$ industrial fermenter (Stanburry and Whitaker, 1984). In addition, these stability properties must be similar for the derivatives of such plasmids carrying a nucleotide insert containing the DNA sequences which it is desired to amplify, express, and the like.

The constraints of biosafety oblige recombinant strains, moreover, to be greatly confined biologically. The biosafety level 1 (BL1) system described in "Guidelines for research involving recombinant DNA molecules" of the NIH of 7th May 1987 corresponds to the smallest constraints. This system, both in Escherichia coli and in Pseudomonas putida, assumes the use of non-conjugative and nonmobilizable plasmids. In effect, if the recombinant microorganism were to be accidentally released into the natural environment, it is imperative that such plasmids cannot be transmitted to other organisms (Trevors et al., 1987).

Now, none of the broad host range plasmids described in the literature fully satisfies these conditions. In the first place, very good segregational stability applying in all cases has never been achieved. In effect, while some of these plasmids are very stable in some hosts, this is not the case in all Gram-negative bacteria. Furthermore, the stability of these plasmids has not, for the most part, been studied after insertion of a DNA fragment, containing, for example, sequences which it is desired to amplify or express. This is the case, in particular, with plasmid pRK290, the stability characters of which have never been studied after insertion of a DNA fragment. Moreover, another feature of the broad host range plasmids described in the prior art lies in the fact that they can mobilize or be mobilized for conjugative transfer from a donor bacterium to a recipient bacterium. This is also the case with plasmid pRK290, which possesses the mob locus. Hence these plasmids are not compatible with the constraints of biosafety since, in the event of accidental discharge of the recombinant organism, the possibility of the plasmid, with the DNA sequences it Carries, being mobilized at a relatively high frequency into other microorganisms cannot be ruled out.

Moreover, the lack of stability of some of these plasmids is also synonymous with low efficiency in the production of proteins or metabolites, and hence with limited interest in industrial fermentation processes.

DETAILED DESCRIPTION OF THE INVENTION

One of the subjects of the present invention lies specifically in a broad host range cloning and/or expression vector, characterized in that it is capable of replicating in almost all Gram-negative bacteria, possesses great segregational stability and is nonmobilized. The subject of the invention is also all derivatives of this vector. Within the meaning of the invention, derivatives of this vector comprise the vectors which, in spite of a few alterations or modifications (deletions, mutations, insertions, etc.) affecting relatively extensive regions, retain the features stated above.

The vectors according to the invention are derived from plasmids of the incompatibility group P having a broad host range in Gram-negative bacteria. More especially, they possess an origin of replication derived from a plasmid belonging to the incompatibility group P. Advantageously, they are derived from plasmid RK2. They combine properties which have never been described for a vector, namely: a broad host range in Gram-negative bacteria, great stability and the absence of mobilization functions.

The great stability of the vectors according to the invention results from the incorporation of a particular nucleotide fragment possessing stabilizing properties. In particular, a particular fragment originating from the natural plasmid RP4 may be used. The cloned fragment, referred to as the par fragment, has been described by Saurugger et al., 1986, as has its capacity to stabilize certain plasmids in E. coli. It has now been found that insertion of the par fragment is accompanied by a very considerable gain in stability, independent of the host organism chosen and of the nature (gene, promoter, etc.) or size of the nucleotide insert. In effect, the segregational stability of the vectors according to the invention, as well as of their derivatives, is higher than that of the RK2 derivatives capable of being used as cloning vectors, this being found in all the Gram-negative bacteria tested.

The loss of the mobilization functions is a second feature of the vectors of the invention. As a result of this, in contrast to plasmids such as pRK290, the vectors according to the invention are not mobilizable from one Gram-negative bacterium to another. They hence form class 1 host-vector systems with these bacteria and comply with industrial regulations. This very advantageous property of the vectors according to the present invention may be obtained, in particular, by deletion of a region carrying the mob locus.

The third property of the vectors according to the invention lies in their capacity to replicate in the majority of Gram-negative bacteria. This property is especially advantageous, since it makes it possible, in particular, to work in *E. coli* in order to carry out the desired constructions, before introducing the vector into the chosen Gram-negative host. It also enables the most suitable host to be chosen in accordance with the desired use of the vectors (amplification, expression, etc.) or with the nature and size of the nucleotide inserts.

In a particular embodiment, the vectors according to the present invention possess a multicloning site with a member of single cloning sites, considerably facilitating the integration of the nucleotide inserts which it is desired to amplify or express.

In another embodiment, the vectors according to the present invention carry a selectable marker such as, in particular, an antibiotic resistance gene. Preferably, they contain the tetracycline resistance gene of RK2. This resistance gene enables the presence of the plasmid to be selected in almost all Gram-negative bacteria. Other resistance genes may be inserted into the vectors described in the present invention, as well as into their derivatives.

A more particular subject of the invention relates to a cloning and/or expression vector having a broad host range in Gram-negative bacteria, characterized in that it is derived from plasmid RK2, is less than 20 Kb in size, contains a DNA fragment carrying the par region of plasmid RP4, does not contain a mob locus and optionally contains a multicloning site and a selectable marker.

The vectors according to the present invention may be used to amplify or express given DNA sequences. A subject of the invention hence relates to the vectors as defined above containing a recombinant DNA fragment.

More especially, the recombinant DNA contains, under the control of sequences for regulation of genetic expression, one or more structural genes coding for one or more given polypeptides. Still according to the invention, the structural genes can be under the control of their own regulator signals, or of different regulator signals. In a preferred embodiment, the sequences for regulation of genetic expression consist of one or more elements chosen from promoters, terminators, signal peptides and ribosome binding sites.

The structural genes which code for a polypeptide can, in particular, be chosen from the genes which code for enzymes, hormones or growth factors. Preferably, they are chosen from the structural gene for albumin, for tPA, for TIMP, for interleukins, for apolipoproteins and for interferons.

In a particular embodiment of the invention, the structural gene(s) is/are gene(s) participating, at genetic or biochemical level, in the biosynthesis of a metabolite, that is to say gene(s) coding for polypeptides involved in the pathway of biosynthesis of a metabolite. In particular, the metabolite can be a vitamin, an amino acid, an antibiotic or any other bacterial metabolite. Preferably, the metabolite is chosen from vitamin B12, biotin, riboflavin, lysine, threonine, methionine, penicillin and tetracycline.

In a preferred embodiment, the vectors according to the invention contain a structural gene coding for a given protein, preceded by signals permitting its expression and, where appropriate, the secretion of the said protein.

Another subject of the invention relates to a method for producing a protein or a metabolite, characterized in that a vector as defined above, containing the structural gene coding for the said protein or one or more of the genes participating, at genetic or biochemical level, in the biosynthesis of the said metabolite, is introduced into a Gram-negative bacterium, this bacterium is cultured under conditions for expression of the said gene(s), and the protein or metabolite produced is recovered.

The vectors described in the present invention may be used on an industrial scale in almost all Gram-negative bacteria. In the case of plasmid pXL1635, it may be used in all Gram-negative bacteria in which plasmid RK2 replicates, that is to say all Gram-negative bacteria except *Myxococcus xanthus, Bradyrhizobium japonicum* and bacteria of the genus Bacteroides (Kües and Stahl, 1989). They may be used in the following manner: one or more DNA fragments carrying the gene(s) which is/are to be, for example, amplified are cloned into a multicloning site, for example; the plasmid thereby constructed is then introduced into the bacterium which it is desired to use at industrial level. A transformation system such as electroporation (Wirth et al., 1989) may be used to introduce the plasmid constructed. The recombinant clones are selected via the resistance supplied by the plasmid. These clones can then be preserved according to the standard techniques for preservation of recombinant strains for industrial application (Standburry and Whitaker, 1984).

A further subject of the invention is the Gram-negative bacteria containing the vectors according to the invention, as well as their uses. In particular, such bacteria may be used to produce a protein or a metabolite, or directly in a bioconversion reaction.

Other subjects and advantages of the present invention will become apparent on reading the examples which follow, which are to be considered as illustrative and non-limiting.

General techniques of cloning, molecular biology and biochemistry

Standard methods of molecular biology, such as caesium chloride/ethidium bromide gradient centrifugation of plasmid DNA, digestion with restriction enzymes, gel electrophoresis, electroelution of DNA fragments from agarose gels, transformation in *E. coli*, nucleic acid precipitation, and the like, are described in the literature (Maniatis et al., 1982, Ausubel et al., 1987). Nucleotide sequences were determined by the chain termination method according to the protocol already published (Ausubel et al., 1987).

Restriction enzymes were supplied by New-England Biolabs (Biolabs), Bethesda Research Laboratories (BRL) or Amersham Ltd (Amersham).

For the ligations, the DNA fragments are separated according to their size on 0.7% agarose or 8% acrylamide gels, purified by electroelution, extracted with phenol, precipitated with ethanol and then incubated in 50 mM Tris-HCl buffer pH 7.4, 10 mM $MgCl_2$, 10 mM DTT, 2 mM ATP in the presence of phage T4 DNA ligase (Biolabs).

If necessary, DNA fragments having protuberant 5' ends are dephosphorylated by treatment with calf intestinal alkaline phosphatase (CIP, Pharmacia) at 37° C. for 30 min in the following buffer: 100 mM glycine, 1 mM $MgCl_2$, 1 mM $ZnCl_2$, pH 10.5. The same technique is used for the dephosphorylation of protuberant 3' or blunt ends, but the treatment is for 15 min at 37° C. and then 15 min at 56° C. The enzyme is inactivated by heating the reaction mixture to 68° C. for 15 min in the presence of 1% SDS and 100 mM NaCl, followed by phenol/chloroform extraction and ethanol precipitation.

Filling-in of protuberant 5' ends is performed with the Klenow fragment of E. coli DNA polymerase I (Biolabs). The reaction is performed at room temperature for 30 min in 50 mM Tris-HCl buffer pH 7.2, 0.4 mM dNTPs, 10 mM MgSO₄, 0.1 mM DTT, 50 µg/ml BSA. Filling-in and/or digestion of protuberant 3' ends is performed in the presence of phage T4 DNA polymerase (Biolabs) according to the manufacturer's recommendations.

Oligonucleotides are synthesized using the chemistry of phosphoramidites protected at the β-position by a cyanoethyl group (Sinha et al., 1984, Giles 1985), with the Biosearch 8600 automatic DNA synthesizer, using the manufacturer's recommendations.

In vitro mutagenesis with oligodeoxynucleotides is performed according to the method developed by Taylor et al., 1985, using the kit distributed by Amersham France, SA.

Deletions performed by means of exonuclease III and S1 nuclease according to the technique of Henikoff, 1984, were carried out using the Promega Erase-a-Base™ System kit (Madison, Wis., USA), following the protocol supplied by the manufacturer.

The ligated DNAs are used to transform the strain rendered competent: E. coli MC 1060 [Δ(lacIOPZYA)ΦX74, galU,galK,strAʳ,hsdR] (Casadaban et al., 1983) and HB101 [hsdS20,supE44,recA13,ara-14, proA2,lacY1, galK2, rpsL20,xyl-5,mtl-1,λ-] (Maniatis et al., 1982) for the plasmids or E. coli TG1 [Δ(lac proA,B),supE,thi,hsdD5/ F'traD36,proA⁺,B⁺,lacIᵠ, lacZΔM15](Gibson, 1984) for the replicative forms of phages derived from bacteriophage M13. The polA strain used is SF800 (Stachel et al., 1985); this strain is resistant to nalidixic acid (Nalʳ). A spontaneously rifampicin-resistant clone (C600 Rifʳ) (50 µg/ml) of the strain C600 [thi-1,thr1,leu-B6,lacY1,tonA21,supE44,λ-] (Maniatis et al., 1982) was used as recipient strain in E. coli-to-E. coli conjugations.

Plasmid DNAs are purified according to the technique of Birnboim and Doly, 1979. Plasmid DNA minipreparations are made according to the protocol of Klein et al., 1980.

LB culture medium is used for the bacteriological part (Maniatis et al., 1982). The strains of Pseudomonas denitrificans SC510 Rifʳ, Agrobacterium tumefaciens C58C9 (Cameron et al., 1989), Pseudomonas putida KT2440 (Bagdasarian et al., 1981), Rhizobium meliloti 102F34 (Leong et al., 1982) are also cultured in LB medium, but the incubation temperature is 30° C.

Conjugations were carried out as described (Ditta et al., 1980). 109 cells of each bacterium participating in the conjugation are filtered off and adsorbed on a 0.45 µm Millipore filter. The filters are then incubated on dishes of LB medium at 37° C. and the cells are thereafter resuspended in 1 ml of 10 mM MgSO₄. Dilutions of the bacterial suspension are then plated out on dishes of LB medium supplemented with suitable antibiotics.

EXAMPLES

The following examples illustrate the invention without limiting it.

Example 1

Construction of plasmid pXL1635

This example illustrates how a multihost vector in Gram-negative bacteria which is non- mobilizable and possesses very great segregational stability can be constructed.

Example 1.1

Production of a pRK290 derivative which has lost the mob locus

This example illustrates how the mob locus of RK2 can be deleted in an RK2 derivative.

The deletion of this locus is made difficult in the sense that no unique restriction site is known in proximity to the mob locus. Were this the case, it would have been possible to carry out an in vitro deletion using, for example, Bal 31 exonuclease as described (Maniatis et al., 1982). In order to be able to carry out this deletion, we introduced a single restriction site at the mob locus of RK2. This was done by directed mutagenesis according to the technique of Taylor et al., 1985. Techniques of directed mutagenesis are carried out only on small fragments. We hence proceeded in three stages: first, subcloning of an RK2 fragment containing the origin of transfer (oriT) into a phage derived from phage M13, followed by directed mutagenesis to introduce a single restriction site; second, the fragment thus mutated is then cloned into plasmid pUC13 (Viera and Messing, 1982), and a cassette carrying a kanamycin resistance gene is thereafter cloned at the restriction site present in the origin of transfer and will then serve as a marker of the mutation introduced; third, the mutated fragment is exchanged by double recombination with the wild-type fragment carried by pRK290. The resulting plasmid is a pRK290 derivative possessing a single restriction site in the origin of transfer. It is hence possible to carry out a mutagenesis by deletion, by reacting exonucleases and then a DNA ligase. These constructions are described in detail below.

The 760-bp HaeII fragment of RK2, which is sufficient in cis to obtain mobilization (Guiney and Yakobson, 1982) was cloned into M13 mp10 (Viera and Messing, 1982). This fragment contains the origin of transfer of RK2 (Guiney and Yakobson, 1983) and, when cloned into a plasmid, renders the latter mobilizable in trans by the tra functions of RK2. This fragment was purified from a HaeII digestion of RK2; the ends were digested with bacteriophage T4 DNA polymerase. Separately, the replicative form of phage M13 mp10 was linearized with digestion with PstI and SstI; the ends were digested with bacteriophage T4 DNA polymerase. The replicative form thereby obtained and the purified fragment were ligated together and then transformed into Escherichia coli TG1 cells rendered competent. The recombinant phages were detected as described (Viera and Messing, 1982). A resulting replicative form was designated pXL1418 (see FIG. 1).

Figure 1:
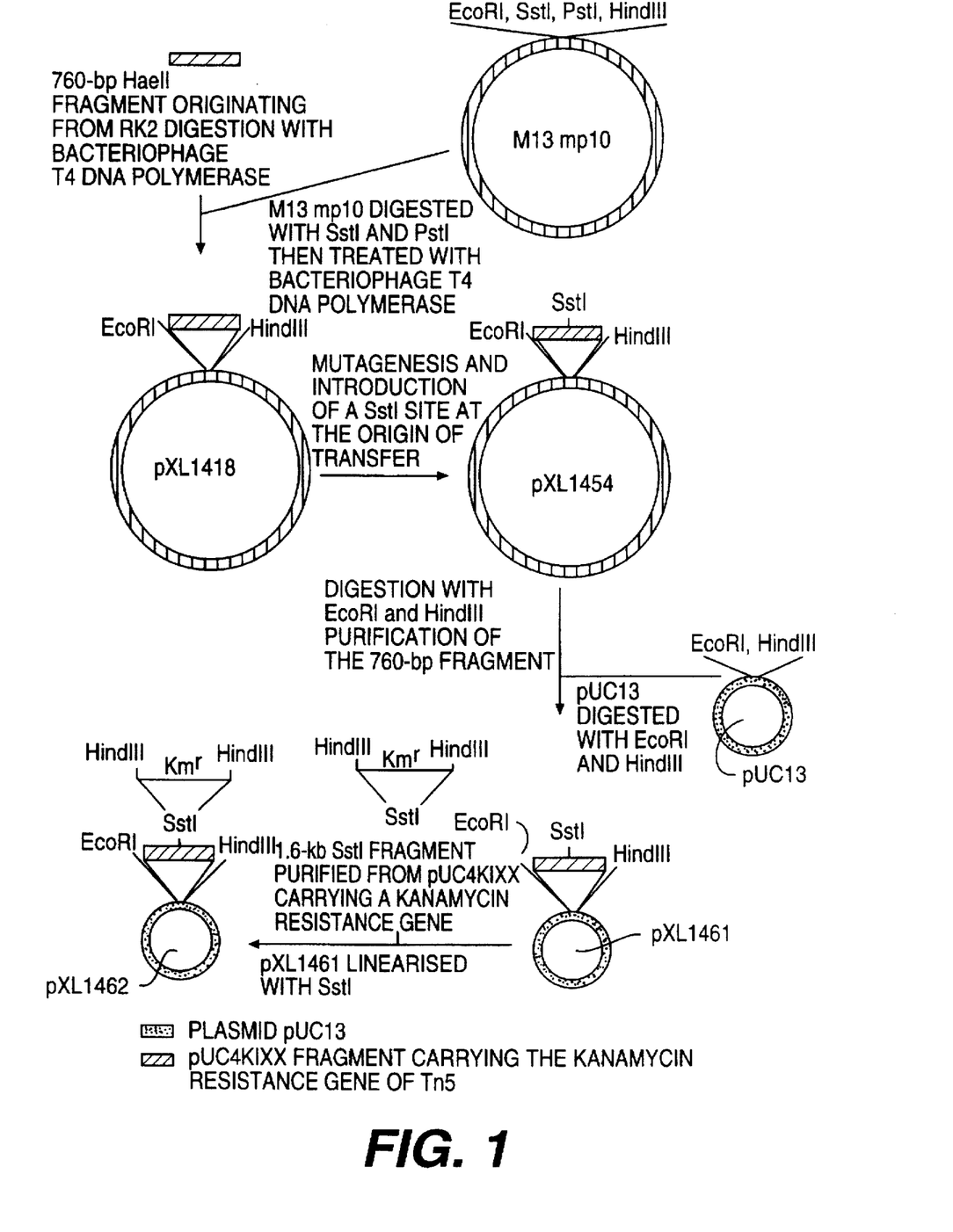
FIG. 1: Construction of pXL 1418, pXL 1454, pXL 1461 and pXL 1462. The constructions are described in detail in the text.
Figure 2:
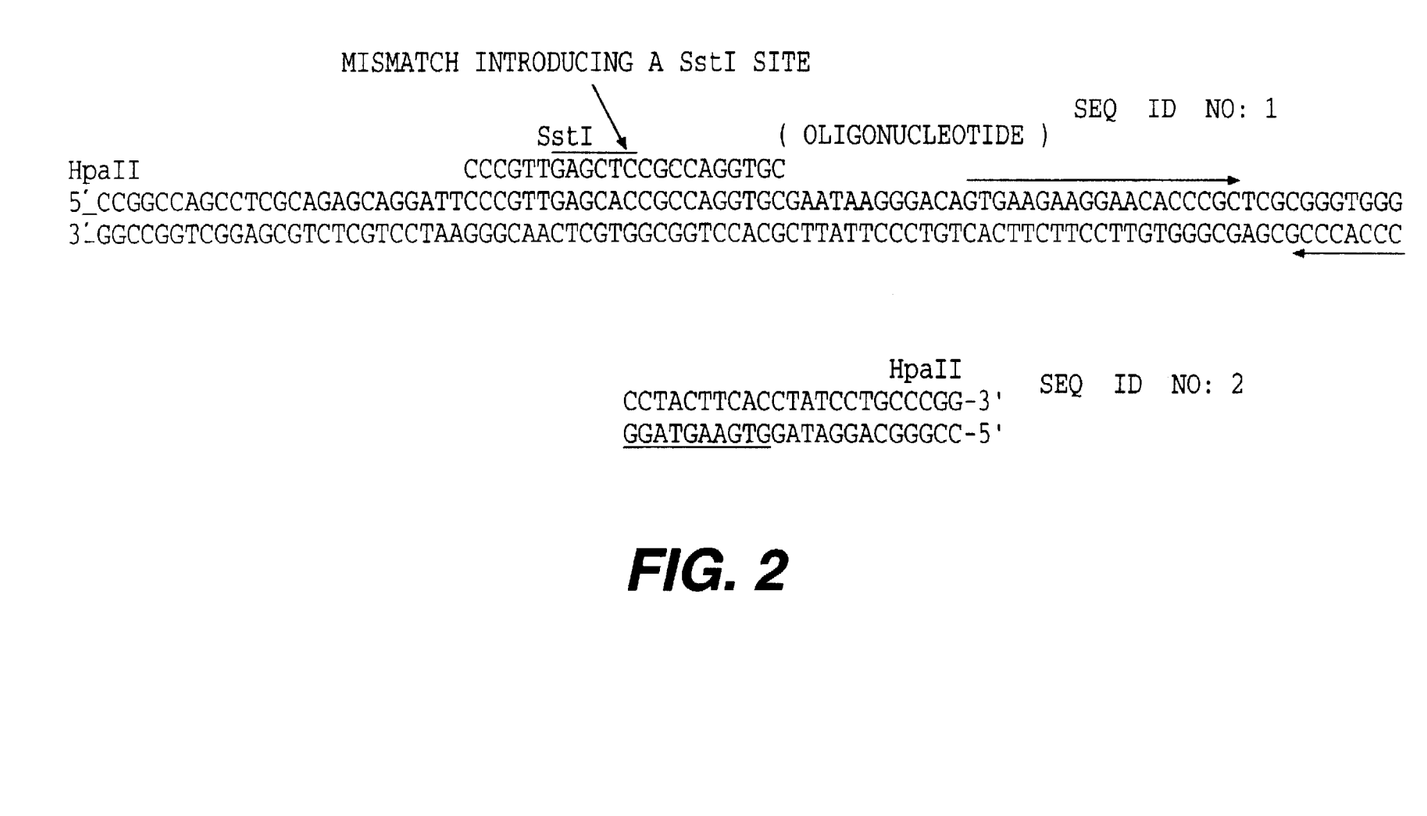
FIG. 2: Sequence of the 110-bp HpaII fragment containing the origin of transfer of RK2 (according to Guiney and Yakobson, 1983). The sequence of the Oligonucleotide used for the mutagenesis is shown, as well as the SstI site which is introduced. The two inverted repeat sequences which must form a hairpin structure are underlined with an arrow.

The sequence of the 112-bp HpaII fragment containing the origin of transfer of RK2 has been published (Guiney and Yakobson, 1983). This fragment is contained in the 760-bp HaeII fragment carried in pXL1418. It is has been observed that there is an inverted repeat sequence capable of forming a hairpin structure, with 19 bp for each repeat sequence (see FIG. 2). A directed mutagenesis according to the method developed by Taylor et al. (1985) was carried out on the single-stranded phage DNA obtained from this replicative form. The oligonucleotide used has the following sequence: 5'-CCC GTT GAG CTC CGC CAG GTG C-3'. The sequence of the 112-bp HpaII fragment and also that of the oligonucleotide are seen in FIG. 2; as shown in this figure, the sequence of the oligonucleotide differs from that of the fragment in only a single nucleotide; this mutation introduces a SstI site. It was first verified that the oligonucleotide was indeed complementary to the single-stranded DNA obtained by infection of E. coli TG1 with the replicative form of pXL1418. To this end, the oligonucleotide in question was used as a nucleotide sequence primer. It was indeed observed that a sequence reaction took place. The nucleotide sequence is read and the first bases do indeed correspond to the sequence of the right-hand end of the upper strand presented in FIG. 2.

Directed mutagenesis was carried out as described above. Mutant clones which do indeed possess a SstI site introduced at the expected position are obtained. One of these replicative forms was designed pXL1454 (see FIG. 1).

pXL1454 is digested with EcoRI and HindIII. The 760-bp fragment is purified, and then ligated with pUC13 digested with EcoRI and HindIII. After transformation, recombinant clones were obtained. One plasmid clone was selected and designated pXL1461 (see FIG. 1).

The next stage consisted in introducing a cassette conferring resistance to an antibiotic at the SstI site in order for a selective marker to be present in the latter. To this end, pXL1461 was linearized with SstI and then ligated with the purified SstI fragment of pUC4KIXX (Pharmacia France, SA). This 1.6-kb fragment carries the kanamycin resistance gene of the transposon Tn5. Recombinant clones were selected after transformation on LB medium supplemented with ampicillin and kanamycin. The plasmid thereby obtained was designated pXL1462 (see FIG. 1).

Figure 3:
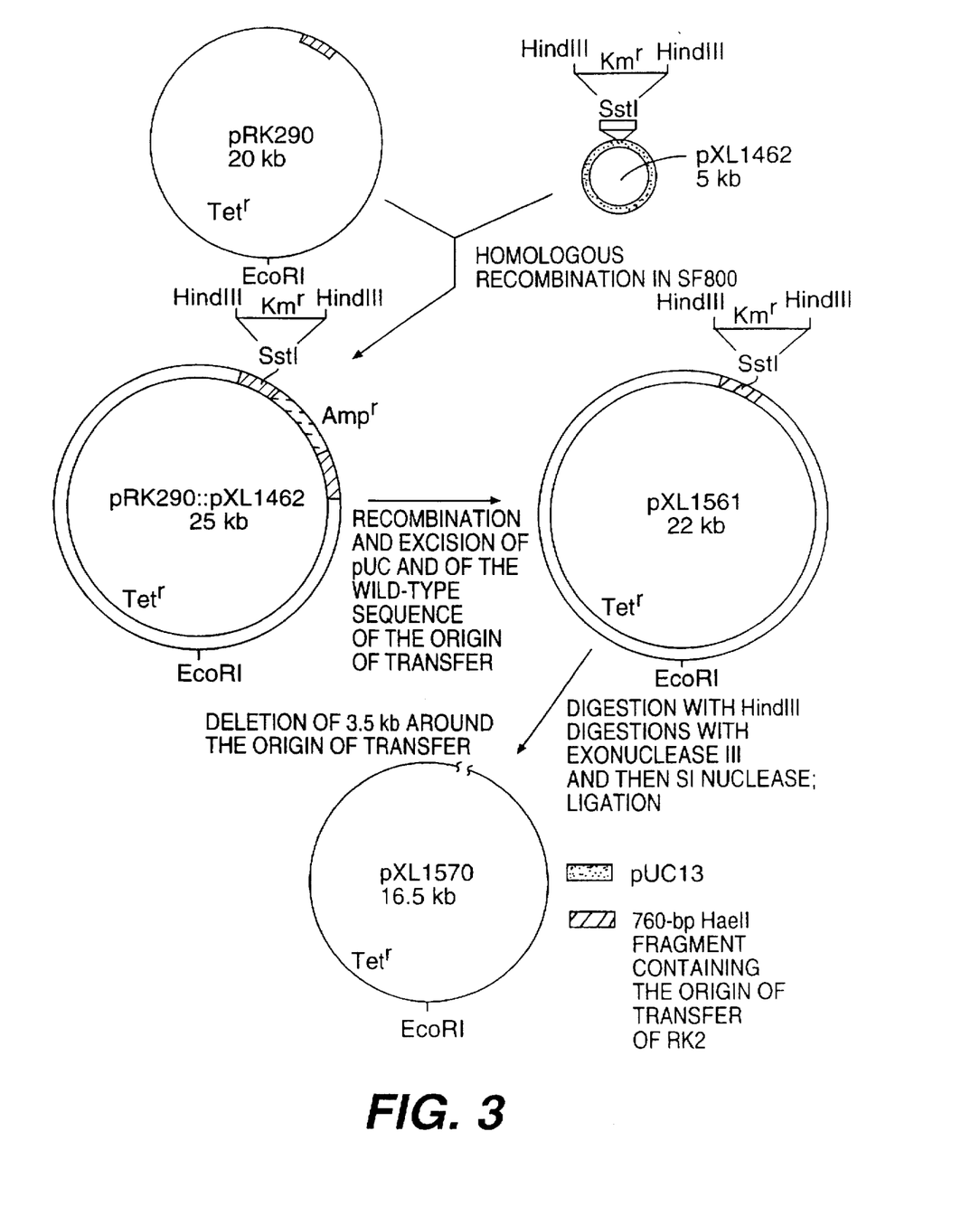
FIG. 3: Construction of pXL1561 and pXL1570. The constructions are described in detail in the text.
Figure 4:
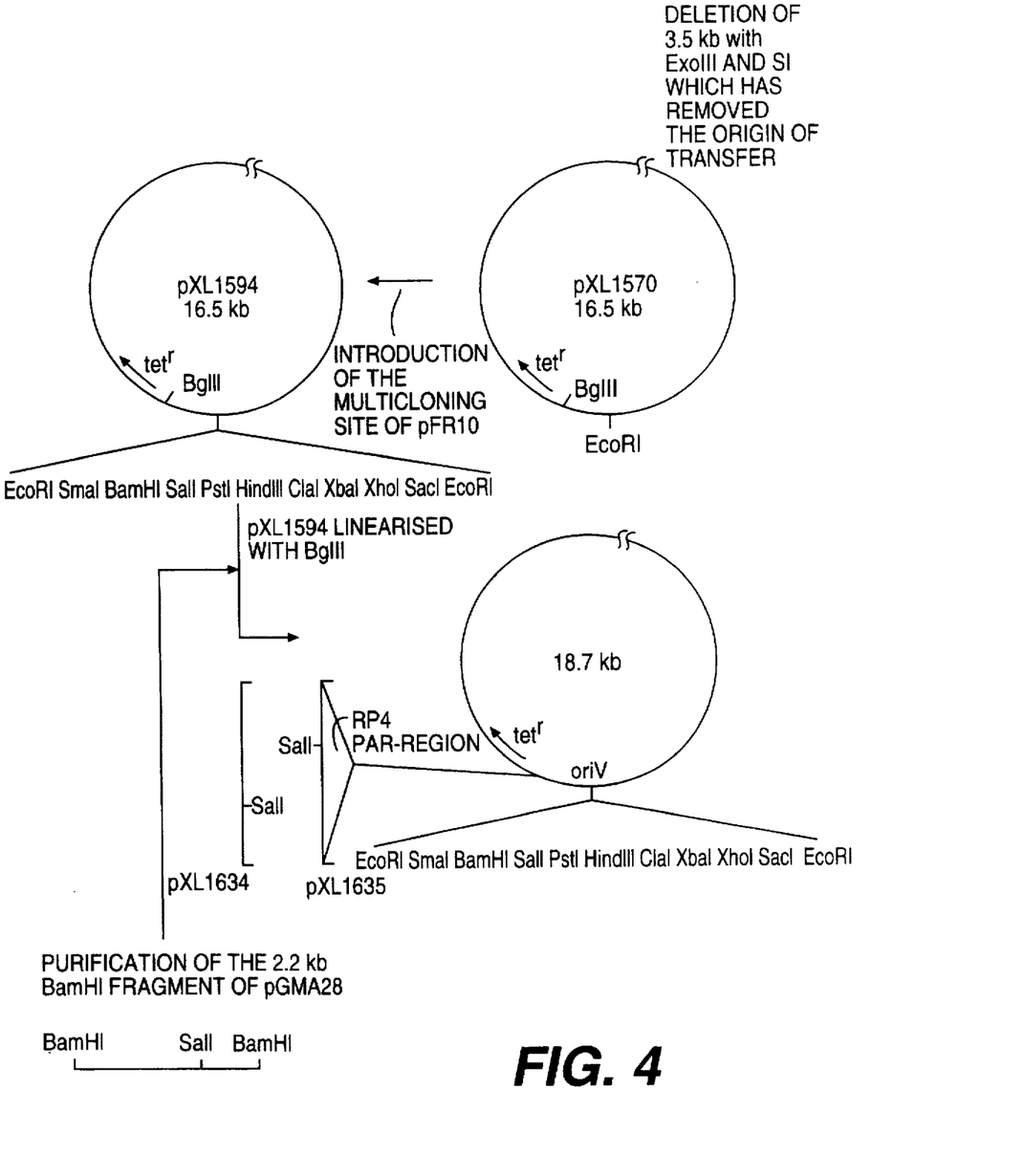
FIG. 4: Construction of pXL1594, pXL1635 and pXL1634. The constructions are described in detail in the text.

Plasmid pRK290 is transformed into an *Escherichia coli* polA strain SF800 (Stachel et al., 1985). In a strain of this kind, plasmids derived from RK2 replicate, since their replication is independent of *E. coli* DNA polymerase I, while pUC13 does not replicate. pXL1462 is then transformed into the strain SF800 pRK290. After transformation, the bacteria are plated out on LB medium supplemented with tetracycline, kanamycin and ampicillin. Since plasmid pXL1462 cannot replicate in this strain, the acquisition of resistances carried by this plasmid can take place only by homologous recombination between the two plasmids. In effect, these two plasmids have in common the 760-bp HaeII fragment carrying the origin of transfer. It is hence possible for there to be homologous recombination between the homologous regions of the two plasmids, resulting in a fusion between the two replicons. The plasmid DNA of a clone resistant to the three antibiotics was analyzed by restriction. Agarose gel analysis proves that it contains only one plasmid. Analysis of this plasmid by restriction digestions shows that pXL1462 has indeed recombined with plasmid pRK290 at the origin of transfer. The plasmid resulting from the fusion of the two replicons carries two origins of transfer of RK2: one wild-type, and one possessing a SstI site introduced by mutagenesis into which a cassette carrying a kanamycin resistance gene has been cloned (see FIG. 3). A clone containing such a plasmid is then cultured via dilution cultures in LB medium supplemented with tetracycline and kanamycin. The absence of ampicillin will make it possible for single-recombination events, with excision of pUC13 carrying the wild-type copy of the 760-bp fragment of the origin of transfer, not to be counterselected. Since pUC13 and the derived plasmids do not replicate, the excised plasmid will be lost immediately. After a series of dilution cultures representing 60 generations, in liquid medium which is selective for pRK290 and for the marker of the mutated origin of replication, the bacteria are plated out on LB medium supplemented with the same antibiotics. 2000 colonies are subcultured on the same medium and on dishes of LB medium supplemented with ampicillin. 2 clones sensitive to ampicillin are obtained. The plasmids carried by these clones are purified and analyzed by restriction. These analyses show that these plasmids correspond exactly to the excision of pUC13 with the wild-type copy of the origin of transfer of RK2. This plasmid is designated pXL1561 (see FIG. 3). Since this plasmid possesses two HindIII sites in the origin of transfer, it is possible to carry out a deletion by digestion with an exonuclease after digestion of the plasmid with HindIII (see FIG. 3). Plasmid pXL1561 was hence digested with HindIII, and a series of dilutions was then carried out by the technique of Henikoff (1984); this technique employs the successive action of exonuclease III and of S1 nuclease; the deletions obtained are two-directional. These deletions are then ligated, and the ligation is transformed into MC1060. The plasmid DNA of transformants thereby obtained is analyzed by restriction digestions. Several clones show they have undergone a deletion at the mob locus. We selected a plasmid which had undergone a deletion of 3.5 kb. This deletion should correspond, if the exonuclease III has digested the DNA of the plasmid with the same kinetics on both sides of the HindIII sites, to a deletion of 1.75 kb on each side of the origin of transfer of the plasmid. The plasmid thereby obtained is designated pXL1570 (see FIG. 3).

pXL1570 possesses EcoRI and BglII as single restriction-sites. We sought to introduce a multicloning site at the EcoRI site in order for the resulting plasmid to contain several cloning sites. Plasmid pFR10 (Shapira et al., 1983), which possesses a multicloning site flanked by two EcoRI sites, is used as the source of a multicloning site. pFR10 is digested with EcoRI, as is pXL1570. The two digestions are ligated, and the ligation is transformed into *E. coli* MC1060. Recombinant clones are obtained, including one, designated pXL1594 (see FIG. 4), in which the orientation of the multicloning site is determined.

Example 1.2

Construction of a nonmobilizable pRK290 derivative possessing the par locus of RK2

This example illustrates how, by cloning a fragment carrying the par locus of RP4 into an RK2 derivative, a plasmid which is more segregationally stable is obtained.

The 2.2-kb BamHI fragment of pGMA28 (Gerlitz et al., 1988) containing the par locus of RP4 is purified, and then ligated with pXL1594 linearized with BglII. The ligation is transformed into *E. coli* MC1060. The plasmid DNA of 24 transformants is analyzed by restriction digestion, and 3 clones are carriers of the 2.2-kb fragment. 2 of them possess the fragment in the same orientation, the third corresponding to the reverse orientation. The plasmid corresponding to the first two clones is designated pXL1635, while that containing the fragment in the other orientation is referred to as pXL1634 (see FIG. 4).

The plasmids thereby obtained are derivatives of RK2, and still more precisely of pRK290, with a deletion of 3.5 kb around the origin of transfer and integration of the par region of RP4 and, optionally, of a multicloning site. The following sites may be used for symmetrical clonings: EcoRI, BamHI, PstI, HindIII, ClaI, XbaI, XhoI and SstI; for asymmetric clonings, EcoRI should be ruled out but the other enzymes may be used.

Example 2

Mobilization of pXL1635

The mobilization of pXL1635 was studied. It is performed on an *E. coli*-to-*E. coli* conjugative transfer. A transfer involving three participants (according to the technique already described by Ditta et al., 1980) was performed using the following strains strain carrying the plasmid to be mobilized: HB101 (pXL1635) or HB101 (pRK290) or HB101 (pXL1570) or HB101 (pUC9tet).

strain containing the "helper" plasmid for the mobilization of the RK2 derivatives: HB101 pRK2013 recipient strain: C600 Rif$^r$.

Plasmid pUC9tet is obtained from Pharmacia France S. A.; it is a nonmobilizable plasmid derived from pBR322, conferring the same resistance as plasmids pRK290, pXL1635 and pXL1570.

The transconjugants are selected on LB medium supplemented with tetracycline and rifampicin. The conjugation frequencies are calculated in the customary manner (Ditta et al., 1980) as the ratio of the number of recipient cells which have actually acquired the resistance of the plasmid to the total number of recipient cells. Conjugation is performed with HB101 as donor strain. The latter is a recA strain, thereby avoiding the homologous recombination which might take place between pRK2013 and pXL1570, pRK290, pXL1635 and pUC9tet since these plasmids have homologous sequences.

Table: Conjugation frequency of RK2 derivatives from *E. coli* HB101 into C600 Rif$^r$. The details of the experiment are given in the text; -: absence of donor plasmid.

| Plasmid | Conjugation frequency |
| --- | --- |
| pXL1635 | <10$^{-5}$ |
| pXL1570 | <10$^{-5}$ |
| pRK290 | 0.2 |
| — | <10$^{-5}$ |
| pUC9tet | <10$^{-5}$ |

As emerges clearly from this table, loss of the mob locus manifests itself in an almost total loss of mobilization (there is at least a factor of 2×10$^4$) between the conjugation frequency of pXL1570 and that of pRK290, whereas these plasmids differ only in the deletion of 3.5 kb). pXL1635 possesses the same properties of mobilization as pXL1570. It is probable, as already described previously, that the conjugation observed here with pXL 1570 and pXL1635 is due to a homologous recombination between these plasmids (which are derived directly from pRK290) and pRK2013, which have regions of homology (Ditta et al., 1980). The control nonmobilizable plasmid pUC9tet is mobilized at frequencies which are not different from those observed for pXL1635 and pXL1570, which shows that these plasmids have indeed lost their property of mobilization and that they can be mobilized only by recombination, even though the donor strains are recA in the experiment described (in this experiment, independent recA recombination must be taking place). Since the mechanism of conjugative transfer of pRK290 is the same between two strains of *E. coli* and between two Gram-negative bacteria, plasmid pXL1635 must be considered to be nonmobilizable irrespective of the host.

Example 3

Introduction of pXL1635 into Gram-negative bacteria other than *Escherichia coli*

This example illustrates how the nonmobilizable plasmid pXL1635 can be introduced into various Gram-negative bacteria.

Since plasmid pXL1635 does not carry an origin of transfer, it cannot be mobilized from *Escherichia coli* to another Gram-negative bacterium. For introduction of pXL1635 into various Gram-negative bacteria, the method of transformation by electroporation (Wirth et al., 1989) is used. The following bacteria are transformed with plasmids pRK290, pXL1570 and pXL1635 by this method:

*Pseudomonas denitrificans* SC510 Rif$^R$

*Agrobacterium tumefaciens* C58C9

*Pseudomonas putida* KT2440

Rhizobium meliloti 102F34

For each bacterium, a recombinant clone is reisolated; the plasmid DNA is purified and is shown by several restriction digestions not to be different from that of the initial plasmid. Plasmid pXL1635 may hence be introduced into Gram-negative bacteria.

Example 4

Stability of pXL1635

This example illustrates the fact that pXL1635 is more stable than pRK290 in various Gram-negative bacteria.

The different recombinant bacteria, as well as the parent strains, are cultured in LB medium without addition of antibiotic. When the stationary phase is reached, a 1/1000 dilution is carried out. These strains are thus cultured on average for 50 generations (.the number of generations is estimated at 0 and is within the range from 40 to 60). Dilutions of the cultures are then plated out on LB agar medium. For each culture, 200 independent clones are subcultured on medium which is selective for the plasmid. The incidence of clones which has lost the resistance, and hence the plasmid, was calculated. This value is recorded in the table below.

Table: Incidence, in %, of loss of plasmids pRK290, pXL1570 and pXL1635 in various Gram-negative bacteria.

| Strains | pRK290 | PXL1570 | pXL1635 |
| --- | --- | --- | --- |
| *Escherichia coli* MC1060 | 2 | 3 | 0 |
| *Pseudomonas denitrificans* SC510Rif$^R$ | 15 | 13 | 1 |
| *Agrobacterium tumefaciens* C58C9 | 25 | 27 | 0 |
| *Pseudomonas putida* KT2440 | 1 | 2 | 0 |
| *Rhizobium meliloti* 102F34 | 2 | 2.5 | 0 |

The values correspond to the incidence, in %, of clones which have lost the resistance of the plasmid after 50 non-selective generations of culture in LB medium.

From this table, it emerges clearly that pXL1635 is much more stable than pRK290 and pXL1570; this property is genuine in all the bacteria studied. The latter two plasmids have the same incidence of clones which have lost the plasmid; the differences observed are not significant from a statistical standpoint. Hence the deletion of 3.5 kb does not affect the properties of replication and stability of pRK290. On the contrary, cloning of the 2.2-kb fragment of pGMA28 brings about a very considerable gain in stability. These results show clearly that plasmid pXL1635 is a plasmid which possesses much more advantageous properties than pRK290 from the standpoint of stability. These advantages are, of course, the same over the other RK2 derivatives which are, according to published data, less advantageous than pRK290 for industrial use (Schmidhauser et al., 1988).

Definition of the terms employed and abbreviations

Recombinant DNA: set of techniques which make it possible either to combine, within the same microorganism, DNA sequences which are not naturally so combined, or specifically to mutagenise a DNA fragment.

ATP: adenosine 5'-triphosphate

BSA: bovine serum albumin

Stop codon: translation termination codon dNTP: 2'-deoxyribonucleoside 5'-triphosphates DTT: dithiothreitol kb: kilobase(s)

bp: base pair(s).

Bibliographic references

Ausubel F. M., R. Brent, R. E. Kinston, D. D. Moore, J. A. Smith, J. G. Seidman and K. Struhl. 1987. Current protocols in molecular biology 1987–1988. John Willey and Sons, New York.

Bagdasarian, J. Frey, and K. Timmis. 1981. Specific-purpose plasmid cloning vectors. II. Broad host range, high copy number. RSF1010-derived vectors, and a host vector system for gene cloning in Pseudomonas. Gene 16, 237–247.

Cameron B. K. Briggs, S. Pridmore, G. Brefort and J. Crouzet. 1989. Cloning and analysis of genes involved in coenzyme B12 biosynthesis in Pseudomonas denitrificans. J. Bacteriol, 171, 547–557.

Casadaban, M. J., A. Martinez-Arias, S. T. Shapira and J. Chou. 1983. β-galactosidase gene fusion for analysing gene expression in Escherichia coli and Yeast. Methods Enzymol. 100, 293–308.

Derbyshire, K. M. and N. S. Willets. 1987. Mobilization of the non-conjugative plasmid RSF1010: a genetic analysis of its origin of transfer. Mol. Gen. Genet., 206, 154–160.

Ditta G., Schmidhauser T., Yakobson E., Lu P., Liang X.-W., Finlay D. R., Guiney D., Helinski D. R., 1985. Plasmids relating to the broad host range Vector pRK290, useful for gene cloning and for monitoring gene expression. Plasmid, 13, 149–154.

Ditta G., Stanfield S., Corbin D., Helinski D. R., 1980. Broad host range DNA cloning system for Gram-negative bacteria: Construction of a gene bank of Rhizobium melitoti. Proc. Natl. Acad. Sci. U.S.A., 77, 7347–7351.

Gerlitz, M., O. Hrabak and H. Schwab. Abstract 8th International Biotechnology Symposium, 1988, A156, p. 129.

Giles, J. W. 1985. Adances in automated DNA synthesis. Am. Biotechnol., Nov./Dec.

Guidelines for research involving recombinant DNA molecules; Notice. National Institute of Health, Federal Register, Vol.51, No.88, 16958–16965.

Guiney, D. G. and E. Yakobson. 1983. Location and nucleotide sequence of the transfer origin of the broad host range plasmid RK2. Proc. Acad. Sci. USA, 80, 3595–3598.

Henikoff S. 1984. Unidirectional digestion with exonuclease III creates targeted breakpoints for DNA sequencing. Gene, 28, 351–359.

Keen, N. T., S. Tamaki, D. Kobayashi and D. Trollinger. 1988. Improved broad host range plasmids for DNA cloning in gram-negative bacteria. Gene, 70, 191–197.

Kües, U. and U. Stahl. 1989. Replication of plasmid in gram-negative bacteria. Mic. Rev., 53, 491–516.

Leong, L. S., G. S. Ditta, and D. R. Helinski. 1982. Identification of a cloned gene coding for δ-aminolevulinic acid synthetase from Rhizobium melitoti. J. Biol. Chem. 257, 8724–8730.

Maniatis, T., E. F. Fritsch, and J. Sambrook. 1982. Molecular cloning: a laboratory manual. Cold Spring Harbor Laboratory, Cold Spring Harbor, N.Y.

Saurugger, P. N., O. Hrabak, H. Schwab and R. M. Lafferty. 1986. Mapping and Cloning of the par-region of broad-host-range plasmid RP4. J. Biotechnol., 4, 333–343.

Schmidhauser, T. J. and D. R. Helinski. 1985. Regions of broad-host-range plasmid RK2 involved in replication and stable maintenance in nine species of gram-negative bacteria. J. Bacteriol., 164, 446–455.

Schmidhauser, T. J., G. Ditta and D. R. Helinski. 1988. Broad-Host-Range plasmid cloning vectors for gram-negative bacteria. In R. L. Rodriguer and D. T. Denhardt (ed.), Vectors, a survey of molecular cloning vectors and their uses, Butterworths, Boston.

Scholz, P. V. Haring, B. Wittman-Liebholt, K. Ashman, M. Bagdasarian and E. Scherzinger. 1989. Complete nucleotide sequence and gene organization of the broad-host-range plasmid RSF1010. Gene, 75, 271–288.

Shapira S. K., J. Chou, F. V. Richaud, and M. C. Casadaban. 1983. New versatile plasmid vector for expression of hybrid proteins coded by a cloned gene fused to lacZ gene sequences encoding enzymatically active carboxy-terminal portion of β-galactosidase. Gene 25, 71–83.

Sinha, N. D., J. Biernat, J. McManus and H. Köster. 1984. Polymer support oligonucleotide synthesis, XVIII: Use of β-cyanoethyl-N,N-dialkylamino-/N-morpholino phosphoramidite of deoxynucleosides for the synthesis of DNA fragments simplifying deprotection and isolation of the final product. Nucl. Acids Res., 12, 4539–4557.

Stachel S. E., G. An, C. Flores and E. W. Nester. 1985. A Tn3 lacZ transposon for the random generation of β-galactosidase gene fusions: application to the analysis of gene expression in Agrobacterium. Embo J., 4, 891–898.

Stanburry, P. F. and A. Whitaker. 1984. Principles of fermentation technology. Pergamon Press, Oxford. Taylor J. W., J. Ott and F. Eckstein. 1985. The rapid generation of oligonucleotide-directed mutations at high frequency using phophorothioate-modified DNA. Nucl. Acid Res., 13, 8764–8765.

Thomas C. M. 1986. Evidence for the involvement of the incC locus of broad host range plasmid RK2 in plasmid maintenance. Plasmid, 16, 15–29.

Trevors, J. T., T. Barkay and A. W. Bourquin. 1987. Gene transfer among bacteria in soil and aquatic environments: a review. Can. J. Microbiol., 33, 191–198.

Viera J. and J. Messing. 1982. The pUC plasmids, an M13mp7-derived system for insertion mutagenesis and sequencing with synthetic universal primers. Gene, 19, 259–268.

Wirth, R., A. Frieseneger and S. F. Fielder. 1989. Transformation of variu-ous species of gram-negative bacteria belonging to 11 different genera by electroporation. Mol. Gen. Genet., 216, 175–177.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

tural gene coding for at least one given polypeptide, wherein said structural gene is under the control of genetic expression sequences.

We claim:
1. A gram negative bacterial vector, comprising:
(a) an origin of replication, wherein said origin of replication is functional in gram negative bacteria;
(b) the par region of plasmid RP4; and
(c) a mob locus, wherein said mob locus contains a deletion of 1.75 kb on each side of OriT.

2. Vector according to claim 1, wherein the mob locus has been deleted.

3. Vector according to claim 1, wherein it contains, in addition, a multicloning site.

4. Vector according to claim 1, further comprising a selectable marker.

5. Vector according to claim 1 further comprising a recombinant DNA fragment comprising at least one struc- 6. Vector according to claim 5, wherein the sequences for regulation of genetic expression are homologous to the structural gene.

7. Vector according to claim 5, wherein the structural gene codes for a polypeptide, wherein said polypeptide is selected from the group consisting of enzymes, hormones, growth factors, and apolipoproteins.

8. Vector according to claim 5, wherein the structural gene codes for a polypeptide involved in the pathway of biosynthesis of a metabolite.

9. Vector according to claim 8 wherein the metabolite is selected from the group consisting of vitamins, antibiotics and amino acids.

10. Vector according to claim 4 wherein the selectable marker is an antibiotic resistance gene.

11. A gram negative bacterial vector for the cloning or expression of genes wherein said vector is obtained by a series of deletions starting from plasmid RK2 and is less than 20 kb in size and comprising: (a) an origin of replication, wherein said origin of replication is functional in gram negative bacteria; (b) the par region of plasmid RP4; (c) a mob locus, wherein said mob locus contains a deletion of 1.75 kb on each side of oriT; and (d) a multicloning site and a selectable marker.

12. Method for producing a protein or a metabolite, comprising introducing a gram negative bacterial vector, comprising:
(a) an origin of replication, wherein said origin of replication is functional in gram negative bacteria; (b) the par region of plasmid RP4; (c) a mob locus, wherein said mob locus contains a deletion of 1.75 kb on each side of OriT; and (d) a recombinant DNA fragment having at least one structural gene coding for the protein sought to be made or at least one gene participating in biosynthesis of the metabolite, wherein said structural gene is under the control of genetic expression sequences into a Gram-negative bacterium;

culturing said bacterium under conditions for expression of said gene, and recovering the protein or a metabolite produced by the bacterium.

* * * * *